United States Patent
Peters et al.

(10) Patent No.: US 7,329,754 B2
(45) Date of Patent: Feb. 12, 2008

(54) 2,5-DIAZABICYCLO[2.2.1]HEPTANE DERIVATIVES

(75) Inventors: Dan Peters, Ballerup (DK); Gunnar M. Olsen, Ballerup (DK); Elsebet Ostergaard Nielsen, Ballerup (DK); Philip K. Ahring, Ballerup (DK); Tino Dyhring Jorgensen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 393 days.

(21) Appl. No.: 10/250,765

(22) PCT Filed: Feb. 28, 2002

(86) PCT No.: PCT/DK02/00133

§ 371 (c)(1),
(2), (4) Date: Apr. 23, 2004

(87) PCT Pub. No.: WO02/070522

PCT Pub. Date: Sep. 12, 2002

(65) Prior Publication Data

US 2004/0181069 A1    Sep. 16, 2004

(30) Foreign Application Priority Data

Mar. 2, 2001 (DK) .............................. 2001 00344

(51) Int. Cl.
*C07D 215/38* (2006.01)
*C07D 265/30* (2006.01)

(52) U.S. Cl. ...................... 546/157; 544/148

(58) Field of Classification Search .............. 546/157; 544/148
See application file for complete search history.

(56) References Cited

U.S. PATENT DOCUMENTS 4,775,668 A * 10/1988 Jefson et al. ............... 514/183

| 5,196,548 A | 3/1993 | Braish et al. |
| 5,478,939 A | 12/1995 | Trybulski et al. |
| 2002/0013309 A1 | 1/2002 | Miller et al. |

FOREIGN PATENT DOCUMENTS

| EP | 1 178 048 A1 | 2/2002 |
| JP | 06-228138 A | 8/1994 |
| WO | WO 96/19479 A1 | 6/1996 |
| WO | WO 00/44755 A1 | 3/2000 |
| WO | WO 00/34284 A1 | 6/2000 |
| WO | WO 00/44755 * | 8/2000 |

OTHER PUBLICATIONS

Kim, J Vet Med Xci, vol. 63(3), pp. 341-342, 2001.*
Lindecrona, Research in Vet Science, vol. 68, pp. 261-264, 2000.*
Bazile, Antimicrobial agents and chemotherapy, Dec. 1992, pp. 2622-2627, 1992.*
Guil et al., Arzneim.-Forsch./Drug Res., vol. 43, No. 1, pp. 56-60 (1993).
Oh, Singapore Med. Journal, vol. 35, pp. 562-564 (1994).

* cited by examiner

*Primary Examiner*—D. Margaret Seaman
(74) *Attorney, Agent, or Firm*—Birch, Stewart, Kolasch & Birch, LLP

(57) ABSTRACT

The present invention relates to novel 2,5-diazabicyclo [2.2.1]heptane derivatives, which are found to be potent modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

5 Claims, No Drawings

2,5-DIAZABICYCLO[2.2.1]HEPTANE DERIVATIVES

This application is the national phase under 35 U.S.C. § 371 of PCT International Application No. PCT/DK02/00133 which has an International filing date of Feb. 28, 2002, which designated the United States of America.

TECHNICAL FIELD

The present invention relates to novel 2,5-diazabicyclo[2.2.1]heptane derivatives, which are found to be potent modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

Indeed several CNS disorders can be attributed to a cholinergic deficiency, a dopaminergic deficiency, an adrenergic deficiency or a serotonergic deficiency.

WO 00/34284 discloses 2,5-diazabicyclo[2.2.1]heptane derivatives which are N-substituted with a monocyclic heterocyclic aromatic group. The 2,5-diazabicyclo[2.2.1]heptane derivatives of WO 00/34284 are reported to have affinity for nicotinic receptors. 2,5-diazabicyclo[2.2.1]heptane derivatives containing bicyclic substituents are not disclosed, and an effect on the monoamine receptors, or the corresponding transporters is not reported.

WO 00/44755 discloses diazabicyclic derivatives useful as nicotinic acetylcholine receptor ligands, including a thieno-pyridinyl derivative, a furo-pyridinyl derivative, a phthalazinyl derivative and a quinolinyl derivative. An effect on the monoamine an effect on the monoamine receptors, or the corresponding transporters is not reported.

SUMMARY OF THE INVENTION

The present invention is devoted to the provision modulators of the monoamine receptors, in particular the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

Accordingly, in its first aspect the invention provides 2,5-diazabicyclo[2.2.1]heptane derivatives represented by the general Formula I

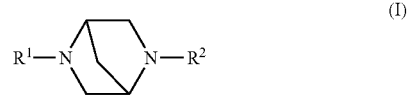

wherein
$R^1$ represents hydrogen, an alkyl group, a cycloalkyl group, an alkenyl group or an aralkyl group; and
$R^2$ represents a bicyclic carbocyclic group or a bicyclic heterocyclic group, which carbocyclic or heterocyclic group is optionally substituted one or more times with substituents selected from the group consisting of alkyl, alkoxy, alkoxyalkyl, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —$CF_3$, —$OCF_3$, —CN, amino, nitro, oxime, alkyloxime, acyloxime, or a group of the formula —(CO)$R^3$, —COO$R^3$, —O(CO)$R^3$, —CON$R^2R^3$, —NH—CO$_2R^2$, —NHCO—$R^2$ or —OCO—N$R^2R^3$; in which formulae $R^2$ and $R^3$ independently of each another represents hydrogen or alkyl;
any of its enantiomers or any mixture of enantiomers, or a pharmaceutically acceptable salt thereof.

In another aspect the invention provides pharmaceutical compositions comprising a therapeutically effective amount of the 2,5-diazabicyclo[2.2.1]heptane derivatives of the invention, any of its enantiomers or any mixture of enantiomers, or a pharmaceutically acceptable salt thereof, together with at least one pharmaceutically acceptable carrier or diluent.

In a third aspect, the invention relates to the of the 2,5-diazabicyclo[2.2.1]heptane derivatives of the invention for the treatment, prevention or alleviation of a disease or a disorder or a condition that is responsive to the action of a monoamine receptor modulator.

In yet a further aspect the invention provides methods for the treatment, prevention or alleviation of disease, disorders or conditions of a living animal body, including a human, which disease, disorder or condition is responsive to the action of a monoamine receptor modulator, which method comprises the step of administering to such a living animal body, including a human, in need thereof a therapeutically effective amount of the 2,5-diazabicyclo[2.2.1]heptane derivatives of the invention.

Other objects of the invention will be apparent to the person skilled in the art from the following detailed description and examples.

DETAILED DISCLOSURE OF THE INVENTION

2,5-diazabicyclo[2.2.1]heptane derivatives

In its first aspect the invention provides novel 2,5-diazabicyclo[2.2.1]heptane derivatives represented by the general Formula I

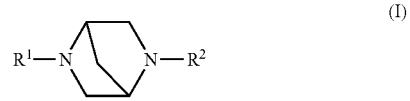

wherein

R¹ represents hydrogen, an alkyl group, a cycloalkyl group, an alkenyl group or an aralkyl group; and R² represents a bicyclic carbocyclic group or a bicyclic heterocyclic group, which carbocyclic or heterocyclic group is optionally substituted one or more times with substituents selected from the group consisting of alkyl, alkoxy, alkoxyalkyl, cycloalkyl, cycloalkoxy, alkoxycycloalkyl, cycloalkoxyalkoxy, cycloalkylalkoxy, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —$CF_3$, —$OCF_3$, —CN, amino, nitro, oxime, alkyloxime, acyloxime, or a group of the formula —(CO)R³, —COOR³, —O(CO)R³, —CONR²R³, —NH—$CO_2$R², —NHCO—R² or —OCO—NR²R³; in which formulae R² and R³ independently of each another represents hydrogen or alkyl;

or any of its enantiomers or any mixture of enantiomers, or a pharmaceutically acceptable salt thereof;

provided, however, that R² does not represent a thienopyridinyl derivative, a furo-pyridinyl derivative, a phthalazinyl derivative or a quinolinyl derivative.

In a preferred embodiment R¹ represents hydrogen or an alkyp group, preferably a $C_{1-4}$-alkyl group, more preferably methyl.

In another preferred embodiment the bicyclic carbocyclic group is indenyl or naphthyl.

In a third preferred embodiment the bicyclic heterocyclic group holds only 5- and/or 6-membered rings.

In a fourth preferred embodiment the bicyclic heterocyclic group is benzimidazolyl, in particular 2,5 or 6-benzimidazolyl;
benzo[b]furanyl, in particular 2,5 or 6-benzimidazolyl;
benzothiazolyl, in particular 5 or 6-benzothiazolyl;
benzo[b]thienyl, in particular 2,5 or 6-benzo[b]thienyl;
cinnolinyl, in particular 6 or 7-cinnolinyl;
1H-indazolyl, in particular 1H-indazol-2,5 or 6-yl;
indolyl, in particular 2,5 or 6-indolyl;
isoindolyl, in particular 2,5 or 6-isoindolyl;
3H-indolyl, in particular 3H-indol-2,5 or 6yl;
indolinyl, in particular 2,5 or 6-indolinyl;
indolizinyl, in particular 2,5 or 6-indolizinyl;
1,8-naphthyridinyl, in particular 1,8-naphthyridin-2,3,6 or 7-yl;
purinyl, in particular 2 or 8-purinyl;
pteridinyl, in particular 2,6 or 7-pteridinyl;
quinolinyl, in particular 2,6 or 7-quinolinyl;
isoquinolinyl, in particular 3,6 or 7-isoquinolinyl;
quinazolinyl, in particular 2,6 or 7-quinazolinyl;
4H-quinolizinyl, in particular 4H-quinolizin-2,3,7 or 8-yl; or
quinoxalinyl, in particular 2 or 6-quinoxalinyl.

In a fifth preferred embodiment the bicyclic heterocyclic group is quinolinyl or benzothiazolyl.

In a sixth preferred embodiment the bicyclic heterocyclic group is optionally substituted once or twice with substituents selected from the group consisting of alkyl, halogen, —$CF_3$, —CN, amino, nitro, and —NHCO—R², wherein R² represents hydrogen or alkyl.

In a seventh preferred embodiment the bicyclic heterocyclic group is optionally substituted once or twice with substituents selected from the group consisting of halogen, —$CF_3$, —CN, amino, and nitro.

In a most preferred embodiment, the 2,5-diazabicyclo[2.2.1]heptane derivative of the invention is 2-(2-Quinolinyl)-(1S,4S)-(+)-2,5-diazabicyclo-[2.2.1]-heptane;
2-(2-Quinolinyl)-5-methyl-(1S,4S)-(+)-2,5-diazabicyclo-[2.2.1]-heptane;
2-(6-Nitro-2-quinolinyl)-(1S,4S)-2,5-diazabicyclo-[2.2.1]-heptane;
2-(6-Nitro-2-quinolinyl)-5-methyl-(1S,4S)-2,5-diazabicyclo-[2.2.1]-heptane;
2-(6-Amino-2-quinolinyl)-5-methyl-(1S,4S)-2,5-diazabicyclo-[2.2.1]-heptane;
2-(6-Acetylamino-2-quinolinyl)-5-methyl-(1S,4S)-2,5-diazabicyclo-[2.2.1]-heptane;
2-(2-Benzothiazolyl)-(1S,4S)-2,5-diazabicyclo-[2.2.1]-heptane; or
2-(2-Benzothiazolyl)-5-methyl-(1S,4S)-2,5-diazabicyclo-[2.2.1]-heptane;

any of its enantiomers or any mixture of enantiomers, or a pharmaceutically acceptable salt thereof.

Any possible combination of two or more of the embodiments described herein is comprised within the scope of the present invention.

Definition of Substituents

In the context of this invention halogen represents fluorine, chlorine, bromine or iodine.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl (allyl); 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of rom two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butynyl; 1-, 2-, 3-, 4-pentynyl, or 1,3-pentynyl; 1-, 2-, 3-, 4-, or 5-henynyl, or 1,3-hexynyl or 1,3,5-hexynyl; 1-, 2-, 3-, 4-, 5- or 6-heptynyl, or 1,3-heptynyl, or 1,3,5-heptynyl; 1-, 2-, 3-, 4-, 5-, 6- or 7-octynyl, or 1,3-octynyl, or 1,3,5-octynyl, or 1,3,5,7-octynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above, an alkenoxy group designates an "alkenyl-O—" group, wherein alkenyl is as defined above, an alkynoxy group designates an "alkynyl-O—" group, wherein alkynyl is as defined above, an alkoxyalkyl group designates an "alkyl-O-alkyl" group, wherein alkyl is as defined above, an alkoxyalkenyl group designates an "alkyl-O-alkenyl" group, wherein alkyl and alkenyl are as defined above, an alkoxy-alkynyl group designates an "alkyl-O-alkynyl" group, wherein alkyl and alkynyl are as defined above, a cycloalkoxy group designates a "cycloalkyl-O—" group, wherein cycloalkyl is as defined above, a alkoxycycloalkyl group designates a "alkyl-O-cycloalkyl-" group, wherein alkyl and cycloalkyl are as defined above, and a cycloalkoxyalkoxy group designates a "cycloalkyl-O-alkyl-O—" group, wherein alkyl and cycloalkyl are as defined above.

In the context of this invention an alkylthio group designates an "alkyl-S—" group (thioalkoxy), wherein alkyl is as defined above, an alkenylthio group designates an "alkenyl-S—" group, wherein alkenyl is as defined above, and an alkynylthio group designates an "alkynyl-S—" group, wherein alkynyl is as defined above.

In the context of this invention an alkylseleno group designates an "alkyl-Se—" group, wherein alkyl is as defined above, an alkenylseleno designates an "alkenyl-Se—" group, wherein alkenyl is as defined above, and an alkynylseleno group designates an "alkynyl-Se—" group, wherein alkynyl is as defined above.

In the context of this invention an alkyloxime group designates a "C=N—O-alkyl" group, wherein alkyl is as defined above, and an acyloxime group designates a "C=N—O—COOH" group or a "C=N—O—CO-alkyl" group, wherein alkyl is as defined above.

In the context of this invention an amino group may be a primary (—NH$_2$), secondary (—NH-alkyl), or tertiary (—N(alkyl)$_2$) amino group, i.e. it may be substituted once or twice with an alkyl group as defined above.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aralkyl group designates an aryl group as defined above, which aryl group is attached to an alkyl group as also defined above. Examples of preferred aralkyl groups of the invention include benzyl.

In the context of this invention a bicyclic carbocyclic group is a bicyclic compound holding carbon only as ring atom. The ring structure may in particular be aromatic (i.e. an aryl group), or saturated or partially saturated. Preferred bicyclic carbocyclic groups of the invention include 5- and 6 membered bicyclic carbocyclic groups. Most preferred bicyclic carbocyclic groups of the invention are the aromatic bicyclic groups and include indanyl, naphthalenyl, azulenyl.

In the context of this invention a bicyclic heterocyclic group is a bicyclic compound, which holds one or more heteroatoms in its ring structure. Preferred heteroatoms include nitrogen (N), oxygen (O), and sulphur (S). The ring structure may in particular be aromatic (i.e. a heteroaryl), or saturated or partially saturated. Preferred bicyclic heterocyclic groups of the invention include 5- and 6 membered bicyclic heterocyclic groups.

In a more preferred embodiment, the bicyclic heterocyclic group is
  benzimidazolyl, in particular 2,5 or 6-benzimidazolyl;
  benzo[b]furanyl, in particular 2,5 or 6-benzimidazolyl;
  benzothiazolyl, in particular 5 or 6-benzothiazolyl;
  benzo[b]thienyl, in particular 2,5 or 6-benzo[b]thienyl;
  cinnolinyl, in particular 6 or 7-cinnolinyl;
  1H-indazolyl, in particular 1H-indazol-2,5 or 6-yl;
  indolyl, in particular 2,5 or 6-indolyl;
  isoindolyl, in particular 2,5 or 6-isoindolyl;
  3H-indolyl, in particular 3H-indol-2,5 or 6-yl;
  indolinyl, in particular 2,5 or 6-indolinyl;
  indolizinyl, in particular 2,5 or 6-indolizinyl;
  1,8-naphthyridinyl, in particular 1,8-naphthyridin-2,3,6 or 7-yl;
  purinyl, in particular 2 or 8-purinyl;
  pteridinyl, in particular 2,6 or 7-pteridinyl;
  quinolinyl, in particular 2,6 or 7-quinolinyl;
  isoquinolinyl, in particular 3,6 or 7-isoquinolinyl;
  quinazolinyl, in particular 2,6 or 7-quinazolinyl;
  4H-quinolizinyl, in particular 4H-quinolizin-2,3,7 or 8-yl; or
  quinoxalinyl, in particular 2 or 6-quinoxalinyl.

Pharmaceutically Acceptable Salts

The 2,5-diazabicyclo[2.2.1]heptane derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

Steric Isomers

The 2,5-diazabicyclo[2.2.1]heptane derivatives of the invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates and Resolutions"*, John Wiley and Sons, New York (1981).

Optical active compounds can also be prepared from optical active starting materials.

Methods of Preparation

The 2,5-diazabicyclo[2.2.1]heptane derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The 2,5-diazabicyclo[2.2.1]heptane derivatives of the present are found to be potent modulators of the monoamine receptors and transporters.

In the context of this invention the term "a monoamine receptor modulator" covers compounds binding to a monoamine receptor, in particular the serotonin receptor, the dopamine receptor and/or the norepinephrine receptor, as well as compounds binding to the biogenic amine transporters for serotonin (5-HT), dopamine (DA) and/or norepinephrine (NE).

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neurodegeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

In this context "treatment" covers treatment, prevention, prophylactics and alleviation of withdrawal symptoms and abstinence as well as treatment resulting in a voluntary diminished intake of the addictive substance.

Pharmaceutical Compositions

In another aspect the invention provides novel pharmaceutical compositions comprising a therapeutically effective amount of the 2,5-diazabicyclo[2.2.1]heptane derivatives of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 2,5-diazabicyclo [2.2.1]heptane derivative together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in drage, in powder, or in liquid form, and parenteral administration, in particular cutaneous, subcutaneous, intramuscular, or intravenous injection. The pharmaceutical composition of the invention can be manufactured by a person skilled in the art by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In another aspect the invention provides methods of the treatment, prevention or alleviation of diseases or disorders or conditions of a living animal body, including a human, which disease or disorder is responsive to the action of a monoamine receptor modulator, and which method comprises the step of administering to such a living animal body, including a human, in need thereof a therapeutically effective amount of the 2,5-diazabicyclo[2.2.1]heptane derivative of the invention.

In the context of this invention the term "treating" covers treatment, prevention, prophylaxis or alleviation, and the term "disease" covers illnesses, diseases, disorders and conditions related to the disease in question.

It is at present contemplated that a suitable dosage lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

General: All reactions involving air sensitive reagents or intermediates were performed under nitrogen and in anhydrous solvents. Magnesium sulphate was used as drying agent in the workup-procedures and solvents were evaporated under reduced pressure.

2-(2-Quinolinyl)-(1S,4S)-2,5-diazabicyclo-[2.2.1]-heptane fumaric acid salt (Compound 1)

A mixture of sodium (0.87 g; 37.9 mmol), methanol (70 ml) and (1S,4S)-(+)-2,5-diazabicyclo-[2.2.1]-heptane dihydrobromide (3.94 g; 15.2 mmol) was stirred at reflux for 1 hour. The mixture was evaporated to dryness. 2-Chloroquinoline (2.48 g; 15.2 mmol) and dioxane (70 ml) was added to the mixture. The mixture was stirred at 100° C. for 2.5 hours. The solvent was evaporated. Aqueous sodium hydroxide (1 M; 50 ml) was added, followed by extraction with diethyl ether (3×50 ml). Chromatography on silica gel with dichloromethane, methanol and conc. ammonia (89:10:1) gave the title compound as free base. Yield 0.89 g (26%). The corresponding salt was obtained by addition of a diethyl ether and methanol mixture (9:1) saturated with fumaric acid. Mp 170.8° C.

2-(2-Quinolinyl)-5-methyl-(1S,4S)-2,5-diazabicyclo-[2.2.1]-heptane (Compound 2)

A mixture of 2-(2-quinolinyl)-(1S,4S)-2,5-diazabicyclo-[2.2.1]-heptane (0.39 g; 1.73 mmol), formaldehyde (2 ml; 37%) and formic acid (2 ml) was stirred at reflux for 24 hours. The solvent was evaporated. Aqueous sodium hydroxide (50 ml; 1 M) was added, followed by extraction with diethyl ether (3×50 ml). Chromatography on silica gel with dichloromethane, methanol and conc. ammonia (89:10:1) gave the title compound as free base. Yield 0.35 g (85%).

2-(6-Nitro-2-quinolinyl)-5-tert-butoxycarbonyl-(1S,4S)-2,5-diazabicyclo-[2.2.1]-heptane (Intermediate compound)

A mixture of 2-chloro-6-nitroquinoline [Lee B S, Lee B C, Jun J-G and Chi D Y; *Heterocycles* 1998 48 (12) 2637-2641] (2.1 g; 10 mmol), tert-butyl-(1S,4S)-(−)-2,5-diazabicyclo[2.2.1]heptane-2-carboxylate (2.0 g; 10 mmol) and dioxane (50 ml) was stirred at reflux for 20 hours. The solvent was evaporated. Aqueous sodium hydroxide (50 ml; 1 M) was added, followed by extraction with diethyl ether (3×50 ml). Chromatography on silica gel with dichloromethane, methanol and conc. ammonia (89:10:1) gave the title compound as free base. Yield 1.6 g (43%).

2-(6-Nitro-2-quinolinyl)-(1S,4S)-2,5-diazabicyclo-[2.2.1]-heptane fumaric acid salt (Compound 3)

2-(6-Nitro-2-quinolinyl)-5-tert-butoxycarbonyl-(1S,4S)-2,5-diazabicyclo-[2.2.1]-heptane (1.6 g; 4.3 mmol) and trifluoroactic acid (5 ml) was stirred for 3 hours. The mixture was evaporated and aqueous sodium hydroxide (50 ml; 10 M) was added. The mixture was extracted with dichloromethane (3×100 ml). The corresponding salt was obtained by addition of a diethyl ether and methanol mixture (9:1) saturated with fumaric acid. Mp 184.0-185.5° C. Yield 1.0 g (86%).

2-(6-Nitro-2-quinolinyl)-5-methyl-(1S,4S)-2,5-diazabicyclo-[2.2.1]-heptane fumaric acid salt (Compound 4)

A mixture of 2-(6-nitro-2-quinolinyl)-(1S,4S)-2,5-diazabicyclo-[2.2.1]-heptane (1.68 g; 6.2 mmol), formic acid (5 ml) and formaldehyde (5 ml) was stirred at reflux for 1.5 hours. The mixture was evaporated. Aqueous sodium hydroxide (50 ml, 1 M) was added and the mixture was extracted with ethyl acetate (3×100 ml). Chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Mp 122.9-123.4° C. Yield 1.76 g (71%).

2-(6-Amino-2-quinolinyl)-5-methyl-(1S,4S)-2,5-diazabicyclo-[2.2.1]-heptane fumaric acid salt (Compound 5)

2-(6-Nitro-2-quinolinyl)-5-methyl-(1S,4S)-2,5-diazabicyclo-[2.2.1]-heptane (0.96 g; 3.4 mmol), palladium on carbon (100 mg; 10%) and ethanol (80 ml) was stirred under hydrogen for 2 hours. The mixture was filtered to remove palladium residues. Yield of free base: 0.79 g (91%). The corresponding salt was obtained by addition of a diethyl ether and methanol mixture (9:1) saturated with fumaric acid. Mp 85.2-87.9° C.

2-(6-Acetylamino-2-quinolinyl)-5-methyl-(1S,4S)-2,5-diazabicyclo-[2.2.1]-heptane fumaric acid salt (Compound 6)

2-(6-Amino-2-quinolinyl)-5-methyl-(1S,4S)-2,5-diazabicyclo-[2.2.1]-heptane (0.395 g; 1.6 mmol), acetic anhydride (180 µl; 1.9 mmol) and dichloromethane (5 ml) was stirred for 3 hours. Aqueous sodium hydroxide (30 ml; 1 M) was added followed by extraction by dichloromethane (2×50 ml). Yield 0.35 g (74%). The corresponding salt was obtained by addition of a diethyl ether and methanol mixture (9:1) saturated with fumaric acid. Mp 92.5-94.4° C.

2-(2-Benzothiazolyl)-5-tert-butoxycarbonyl-(1S,4S)-2,5-diazabicyclo-[2.2.1]-heptane (Intermediate compound)

2-Chlorobenzothiazole (2.57 g; 15.1 mmol) tert-butyl(1S,4S)-(−)-2,5-diazabicyclo-[2.2.1]heptane-2-carboxylate (2.0 g; 10.1 mmol) and dioxane (10 ml) was stirred at reflux for 19 days. Aqueous sodium hydroxide (50 ml; 1 M) was added. The mixture was extracted with ethyl acetate (2×50 ml). Chromatography on silica gel with a mixture of ethyl acetate and petroleum (1:3), gave the title compound as free base (oil). Yield 1.7 g (57%).

2-(2-Benzothiazolyl)-(1S,4S)-2,5-diazabicyclo-[2.2.1]-heptane fumaric acid salt (Compound 7)

2-(2-Benzothiazolyl)-5-tert-butoxycarbonyl-(1S,4S)-2,5-diazabicyclo-[2.2.1]-heptane (1.8 g; 5.4 mmol), triflouroacetic acid (4.2 ml; 54 mmol) and dichloromethane (20 ml) was stirred overnight. Aqueous sodium hydroxide (50 ml; 1 M) was added. The mixture was extracted with dichloromethane (3×50 ml). The corresponding salt was obtained by addition of a diethyl ether and methanol mixture (9:1) saturated with fumaric acid. Mp 177.8-194.3° C.

2-(2-Benzothiazolyl)-5-methyl-(1S,4S)-2,5-diazabicyclo-[2.2.1]-heptane fumaric acid salt (Compound 8)

A mixture of 2-(2-benzothiazolyl)-(1S,4S)-2,5-diazabicyclo-[2.2.1]-heptane (0.64 g; 2.77 mmol), formic acid (5 ml) and formaldehyde (5 ml) was stirred at reflux for 24 hours. Aqueous sodium hydroxide (50 ml; 1 M) was added and the mixture was extracted with dichloromethane (3×50 ml). Chromatography on silica gel with dichloromethane, methanol and conc. ammonia (89:10:1) gave the title compound as free base. Yield 0.19 g (28%). The corresponding salt was obtained by addition of a diethyl ether and methanol mixture (9:1) saturated with fumaric acid. Mp 170.8-181.0° C.

Example 2

Biological Activity

In this example the biological activity of the compounds of the invention are determined using a serotonin transporter/uptake assay. Serotonin transporters/uptake sites on nerve terminals presumably function to terminate neuronal signaling by removing serotonin from the synaptic cleft. The activity of the serotonin transporter integral protein can be measured in vitro by synaptosomal uptake of $^3$H-5-hydroxytryptamine.

Tissue Preparation

Preparations are performed at 0-4° C. Cerebral cortices from male Wistar rats (150-200 g) are homogenized for 5-10 seconds in 100 volumes of ice-cold 0.32 M sucrose containing 1 mM pargyline, and using a motor driven teflon pestle in a glass homogenizing vessel.

Monoamine oxidase activity becomes inhibited by pargyline.

The homogenate is centrifuged at 1000×g for 10 minutes. The resulting supernatant is subjected to centrifugation at 27,000×g for 50 minutes, and the supernatant is discarded. The pellet (P$_2$) is re-suspended in oxygenated (equilibrated with an atmosphere of 96% O$_2$: 4% CO$_2$ for at least 30 minutes) Krebs-Ringer incubation buffer (1000 ml per g of original tissue) at pH 7.2, containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 1 mM CaCl$_2$, 10 mM glucose and 1 mM ascorbic acid.

Assay

Aliquots of 4.0 ml tissue suspension are added to 100 µl of test solution and 100 µl of $^3$H-5-HT (1 nM, final concentration), mixed and incubated for 30 minutes at 37° C. Non-specific uptake is determined using Citalopram (1 µM, final concentration; Available from H. Lundbeck, Denmark), a serotonin reuptake inhibitor.

After incubation the samples are poured directly onto Whatman GF/C glass fibre filters under suction. The filters are washed three times with 5 ml of ice-cold 0.9% (w/v) NaCl solution.

The amount of radioactivity on the filters is determined by conventional liquid scintillation counting. Specific uptake is calculated as the difference between total uptake and non-specific uptake.

Results 25-75% inhibition of specific binding must be obtained, before calculation of an IC$_{50}$.

The test value is presented as IC$_{50}$ (the concentration (µM) of the test substance which inhibits the specific binding of $^3$H-5-HT by 50%), calculated according to the following equation:

$$IC_{50} = \text{(applied test substance concentration, }\mu M\text{)} \times \frac{1}{\left(\frac{C_o}{C_x} - 1\right)}$$

where $C_o$ is specific binding in control assays and $C_x$ is the specific binding in the test assay (the calculations assume normal mass-action kinetics).

The results of this experiment are presented in Table 1, below.

TABLE 1

| Compound No. | Serotonin uptake IC$_{50}$ (µM) |
|---|---|
| 1 | 0.088 |
| 2 | 0.13 |
| 3 | 0.00024 |
| 4 | 0.0034 |
| 5 | 0.84 |
| 7 | 0.35 |

The invention claimed is:

1. A 2,5-diazabicyclo[2.2.1]heptane derivative represented by the general Formula I

(I)

wherein

R$^1$ represents hydrogen, an alkyl group, a cycloalkyl group, an alkenyl group or a benzyl group; and R$^2$ represents a 2-quinolinyl or a benzothiazolyl, which heterocyclic group is optionally substituted one or more times with substituents selected from the group consisting of alkyl, alkoxy, alkoxyalkyl, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulae R$^2$ and R$^3$ independently of each another represents hydrogen or alkyl;

any of its enantiomers or any mixture of enantiomers, or a pharmaceutically acceptable salt thereof.

2. The 2,5-diazabicyclo[2.2.1]heptane derivative of claim 1, wherein R$^1$ represents hydrogen or an alkyl group.

3. The 2,5-diazabicyclo[2.2.1]heptane derivative of claim 1, wherein the bicyclic heterocyclic group is optionally substituted once or twice with substituents selected from the group consisting of alkyl, halogen, —CF$_3$, —CN, amino, nitro, and —NHCO—R$^2$, wherein R$^2$ represents hydrogen or alkyl.

4. The 2,5-diazabicyclo[2.2.1]heptane derivative of claim 1, which is 2-(2-Quinolinyl)-(1S,4S)-(+)-2,5-diazabicyclo-[2.2.1]-heptane;

2-(2-Quinolinyl)-5-methyl-(1S,4S)-(+)-2,5-diazabicyclo-[2.2.1]-heptane;

2-(6-Nitro-2-quinolinyl)-(1S,4S)-2,5-diazabicyclo-[2.2.1]-heptane;

2-(6-Nitro-2-quinolinyl)-5-methyl-(1S,4S)-2,5-diazabicyclo-[2.2.1]-heptane;

2-(6-Amino-2-quinolinyl)-5-methyl-(1S,4S)-2,5-diazabicyclo-[2.2.1]-heptane;

2-(6-Acetylamino-2-quinolinyl)-5-methyl-(1S,4S)-2,5-diazabicyclo-[2.2.1]-heptane;

2-(2-Benzothiazolyl)-(1S,4S)-2,5-diazabicyclo-[2.2.1]-heptane; or 2-(2-Benzothiazolyl)-5-methyl-(1S,4S)-2,5-diazabicyclo-[2.2.1]-heptane;

any of its enantiomers or any mixture of enantiomers, or a pharmaceutically acceptable salt thereof.

5. A pharmaceutical composition comprising a therapeutically effective amount of a 2,5-diazabicyclo[2.2.1]heptane derivative of claim 1, any of its enantiomers or any mixture of enantiomers, or a pharmaceutically acceptable salt thereof, together with at least one pharmaceutically acceptable carrier or diluent.

* * * * *